United States Patent [19]

Scherrer

[11] 4,208,336

[45] Jun. 17, 1980

[54] CERTAIN 3-BROMOMETHYLPHENYL-2-BROMO-BENZOFURANS

[75] Inventor: Robert A. Scherrer, White Bear Lake, Minn.

[73] Assignee: Riker Laboratories, Inc., Northridge, Calif.

[21] Appl. No.: 937,072

[22] Filed: Aug. 28, 1978

Related U.S. Application Data

[60] Division of Ser. No. 842,234, Oct. 14, 1977, Pat. No. 4,124,605, which is a division of Ser. No. 724,716, Sep. 20, 1976, Pat. No. 4,066,782, which is a continuation-in-part of Ser. No. 616,276, Sep. 24, 1975, abandoned.

[51] Int. Cl.$^2$ ........................................... C07D 307/82
[52] U.S. Cl. ............................................. 260/346.22
[58] Field of Search ................................... 260/346.22

[56] References Cited

U.S. PATENT DOCUMENTS 3,917,654  11/1975  Petracek .......................... 260/346.22

Primary Examiner—John M. Ford
Assistant Examiner—Bernard Dentz
Attorney, Agent, or Firm—Cruzan Alexander; Donald M. Sell; Donald C. Gipple

[57] ABSTRACT

Optionally substituted (2-nitro-3-benzofuranyl)phenylacetic acids which are active as antimicrobial agents, processes for their preparation and intermediates therefor are described.

2 Claims, No Drawings

CERTAIN 3-BROMOMETHYLPHENYL-2-BROMO-BENZOFURANS

This is a division of copending application Ser. No. 824,234 filed Oct. 14, 1977 now U.S. Pat. No. 4,124,605, Ser. No. 842,234 being a division of copending application Ser. No. 724,716 filed Sept. 20, 1976 (now U.S. Pat. No. 4,066,782), Ser. No. 724,716 being a continuation-in-part of copending application Ser. No. 616,276 field Sept. 24, 1975 (now abandoned).

FIELD OF THE INVENTION

This invention relates to a class of 3-phenylbenzofuran compounds which are substituted on the 3 or 4 position of the phenyl ring by a lower alkanoic acid group or an ester or pharmaceutically acceptable salt thereof.

BACKGROUND OF THE INVENTION

3-Phenylbenzofuranylalkanoic acid and -alkenoic acids and certain derivatives thereof have been reported, for example in U.S. Pat. Nos. 3,682,976 and 3,862,134 as having antiinflammatory activity. The compound 2-nitro-3-phenylbenzofuran has been reported, although no physiological activity has been reported prior to the present invention. Certain neutral 2-nitrobenzofurans are known as antibacterial agents, for example, see French Pat. No. 2,081,585 and several publications by Rene Royer, et al. Acidic compounds combining the structural features of the compounds of the present invention have not previously been described.

SUMMARY OF THE INVENTION

The present invention relates to optionally substituted (2-nitro-3-benzofuranyl)phenylacetic acids and esters and pharmaceutically acceptable salts thereof which are active as antimicrobial agents.

It is therefore an object of the invention to provide compounds which are active antimicrobial agents.

It is a further object of the invention to provide processes for preparing the compounds of the invention.

It is a further object of the invention to provide a method for controlling microbes.

It is a further object of the invention to provide a method for controlling bacteria.

It is a further object of the invention to provide a method for conrolling fungi.

It is a further object of the invention to provide a method for controling protozoa.

It is a further object of the invention to provide a method for controlling trichomonads.

It is another object of the invention to provide antimicrobial compositions containing (2-nitro-3-benzofuranyl)phenylacetic acids and esters and pharmaceutically acceptable salts thereof as active ingredients therein.

It is another object of the invention to provide novel intermediates in the preparation of the antimicrobial agents of the invention and processes using the novel intermediates to prepare the active agents.

Still other objects of the invention will be made apparent by the following specification.

DETAILED DESCRIPTION OF THE INVENTION

The present invention relates to a class of compounds of the formula:

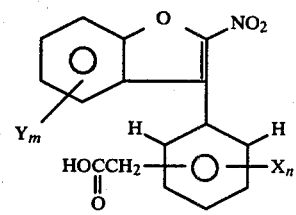

wherein X is halogen, lower aklkyl, lower alkoxy or trifluoromethyl, Y is methyl, methoxy or halogen and m and n are independently zero, one or two, and esters and pharmaceutically acceptable salts thereof. When m or n is zero, the indicated ring positions are unsubstituted. The term "lower" whenever used in this specification indicates groups containing from one to four carbon atoms.

The free acids are ordinarily white or yellowish to brown crystalline or amorphous materials when purified. They are substantially insoluble in water or aliphatic hydrocarbons and are more soluble in lower alcohols, halogenated solvents, benzene, dimethylformamide and the like. The esters are generally somewhat more soluble in organic solvents. The alkali metal salts have appreciable solubility in water and lower alcohols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animals. The free acids are presently preferred for many purposes due to their generally higher levels of antimicrobial activity in vitro. For applications in which water solubility is of importance, the salts are ordinarily used.

The presently most preferred compound (which has a broad spectrum of antimicrobial activity and good therapeutic ratio, $LD_{50}/ED_{50}$) is 4-(2-nitro-3-benzofuranyl)phenylacetic acid.

Alkalki metal, alkaline earth, aluminum, iron and other metal and amine salts are often the equivalents of the corresponding acid-form compounds, and offer advantages in solubility, absorption, persistence, formulation and the like. The salts are of particular interest for topical use, for example in opthalmic and dermatologic formulations. The alkali metal salts (e.g. the sodium and potassium salts) are presently preferred. The esters are also useful for modifying solubility, persistence, absorption and other properties of the compounds under conditions of use. Examples of esters are ethyl, and other lower alkyl esters, diethylaminoethyl, 2-hydroxyethyl, glyceryl, and methoxymethyl.

The free acid compounds of the invention are prepared by several methods using known starting materials including:

A. directly nitrating the 2 position of a compound of the formula

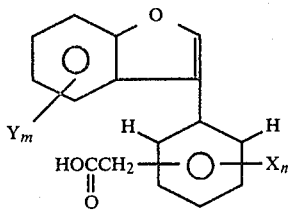

B. specifically halogenating the 2 position of a compound of formula II to form an intermediate compound of the formula

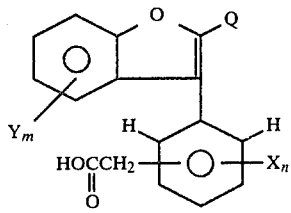

wherein Q is bromine or iodine followed by selectively displacing the 2-halogen atom by a nitro group, or C. the acid hydrolysis of a corresponding compound of the formula

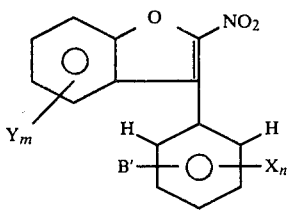

wherein B' is an acetic ester group or a cyanomethyl group.

The direct nitration process (process A) can be carried out with fuming nitric acid in acetic acid or acetic anhydride or with dinitrogen tetroxide in an inert solvent such as dichloromethane. In order to avoid aromatic nitration, moderate temperatures of 0° to 30° C. are generally used.

The halogenation step of process B may be bromination or iodination. The bromination can be carried out using bromine water, N-bromosuccinimide or preferably bromine in a suitable solvent such as dichloromethane or acetic acid. Bromination is carried out under mild conditions, e.g. 0° to 30° C. to avoid aromatic bromination. The bromo compound may be isolated or used without isolation. Isolation may be carried out by extraction, precipitation by the addition of a solvent such as water, evaporation of volatile reaction components, etc. The iodination is carried out e.g. with molecular iodine in the presence of yellow mercuric oxide in an inert solvent such as benzene. Generally these reactions are carried out at about 25° 125° C., for example at the reflux temperature of the solvent.

In the final step of process B, the 2-halo substituent can be displaced by means of selected nitrating agents, such as strong nitric acid solution, for example 70% aqueous nitric acid, dinitrogen tetroxide in e.g. acetic acid or dichloromethane solution or a mixture of sodium nitrite and a strong acid. When 70% nitric acid is used as the nitrating reagent for 2-halo derivatives, preferably about two to three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml per gram required) and concentrated sulfuric acid is added, from two to ten milliliters per gram of benzofuran. Sodium nitrite is then added to the solution. From two to five moles of nitrite per mole of benzofuran derivative is used. The reaction temperature is about 20° to 100° C., and preferably about 55° C. The sodium nitrite can be replaced in this reaction by other metal nitrites such as potassium nitrite.

A combination of nitrogen tetroxide in an inert solvent in the presence of an alkene is one presently preferred nitration method according to process B, with acetic acid and dichloromethane as the preferred solvents. For example, two to five liters of acetic acid per mole of benzofuran or halobenzofuran derivative are generally used. At least one mole of nitrogen tetroxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of $BrNO_2$ and minimize bromination as a side reaction. Cyclohexene is satisfactory for this use. Preferably equimolar amounts of alkene and nitrogen tetroxide are used. The olefin is chosen to be less reactive to $N_2O_4$ than the benzofuran but more reactive to $BrNO_2$ than the benzofuran. An acidic olefin, e.g. 3-cyclohexene carboxylic acid is advantageous when the nitrated product is neutral. The temperature of these reactions is generally about 0° to 80° C., preferably 20° to 45° C. for bromine exchange and about 0° to 25° C. for iodine exchange and direct nitration. When 2-idobenzofurans are used, the olefin is not required (since the iodine is generally unreactive to the benzofuran under the reaction conditions) and only one-half mole of $N_2O_4$ is theoretically then required.

The 2-nitro-3-phenylbenzofuran acid esters for use in process C are prepared by nitration of the corresponding 2-halo-3-phenylbenzofuran acid esters. These esters, preferably lower alkyl esters, are readily hydrolyzed by conventional acid hydrolysis.

The novel 2-nitro-3-(cyanomethylphenyl)benzofurans for use in process C are prepared (a) from novel 2-nitro-3-(bromomethylphenyl)benzofurans by displacement of bromine with cyanide in inert solvents such as ketones, alcohols and N,N-dimethulformamide, generally at the reflux temperature of the solvent or at about 100° C. or (b) by displacement of halogen from 2-bromo-3-(cyanomethylphenyl)benzofurans using techniques and conditions described hereinabove. Hydrolysis of 2-nitro-3-(cyanomethylphenyl)-benzofurans is effected under acidic conditions, for example in aqueous sulfuric acid at 60° to reflux.

Hydrolysis of 2-halo-3-(cyanomethylphenyl)-benzofurans to produce the intermediates for process B is effected under strongly acidic or basic conditions, for example in aqueous sulfuric acid at 60° to 175° C. or in aqueous alcoholic alkali at its reflux temperature.

The (2-nitro-3-benzofuranyl)phenylacetic acid esters are prepared either by nitration of the corresponding 2-halo compounds or by esterification of (2-nitro-3-benzofuranyl)phenylacetic acid derivatives such as acyl halides with alcohols or acid salts with alkyl halides. The salts of the (2-nitro-3-benzofuranyl)phenylacetic acids are prepared by reaction of the corresponding acids with an organic or inorganic base in a suitable solvent. The acyl halides of the (2-nitro-3-benzofuranyl)-phenylacetic acids are readily prepared by reaction of the acids with thionyl chloride, generally in a non-reactive solvent such as dichloromethane or benzene.

The (3-benzofuranyl)phenylacetic acids and esters used as intermediates for the preparation of compounds of the invention are novel compounds. They are prepared from known starting materials by an extended synthetic sequence, which is illustrated below.

Step ② is the formation of an α-bromoacetophenone derivative, and bromination proceeds readily in the expected manner in an inert solvent such as dichloromethane.

In step ③ equimolar amounts of known phenols and the optionally substituted ethyl α-bromoacetophenylacetates prepared in step ②, or an excess of the phenol, are reacted in the presence of a base. Generally the base is a weak inorganic base such as an alkali metal carbonate. A solvent is used, for example glyme, tetrahydrofuran, benzene, ethanol, pyridine and the like and an inert atmosphere may be used. The reaction is carried out at from about 50° C. to the reflux temperature. The product is isolated by conventional methods such as extraction or elution chromatography.

In step ④ the products of step ③ are cyclized by heating in polyphosphoric acid. The product benzofurans are novel and are easily separated and isolated by dilution of the reaction mixture with water and filtration or extraction.

In some instances the acid intermediate may be preferred for use in subsequent synthetic steps. Step ⑤ illustrates hydrolysis of the ester to the acid. This is generally done using conventional acid or base hydrolysis conditions.

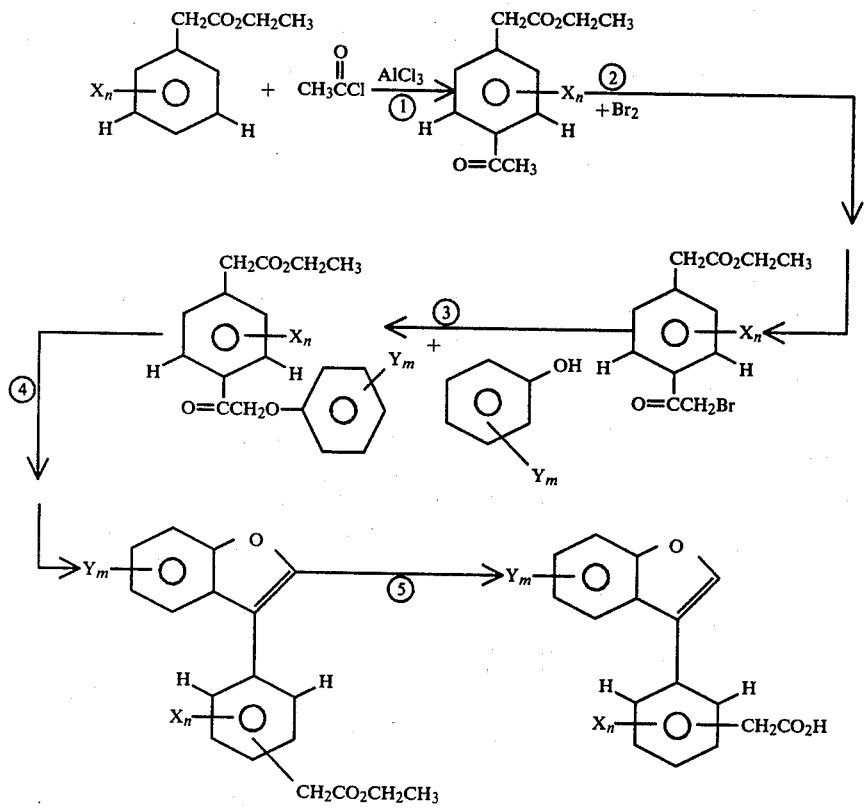

Step ① is the Friedel-Crafts reaction of an ethyl phenylacetate with acetyl chloride using aluminum chloride as catalyst. Typical solvents inert to these reaction conditions, including dichloroethane, are used. Substituted phenylacetic acids and their esters and methods for their synthesis are known to the art.

The (2-nitro-3-benzofuranyl)alkane cyanides used as intermediates for the preparation of compounds of the invention are novel compounds. They are prepared from known starting materials by the reaction sequence which is illustrated below.

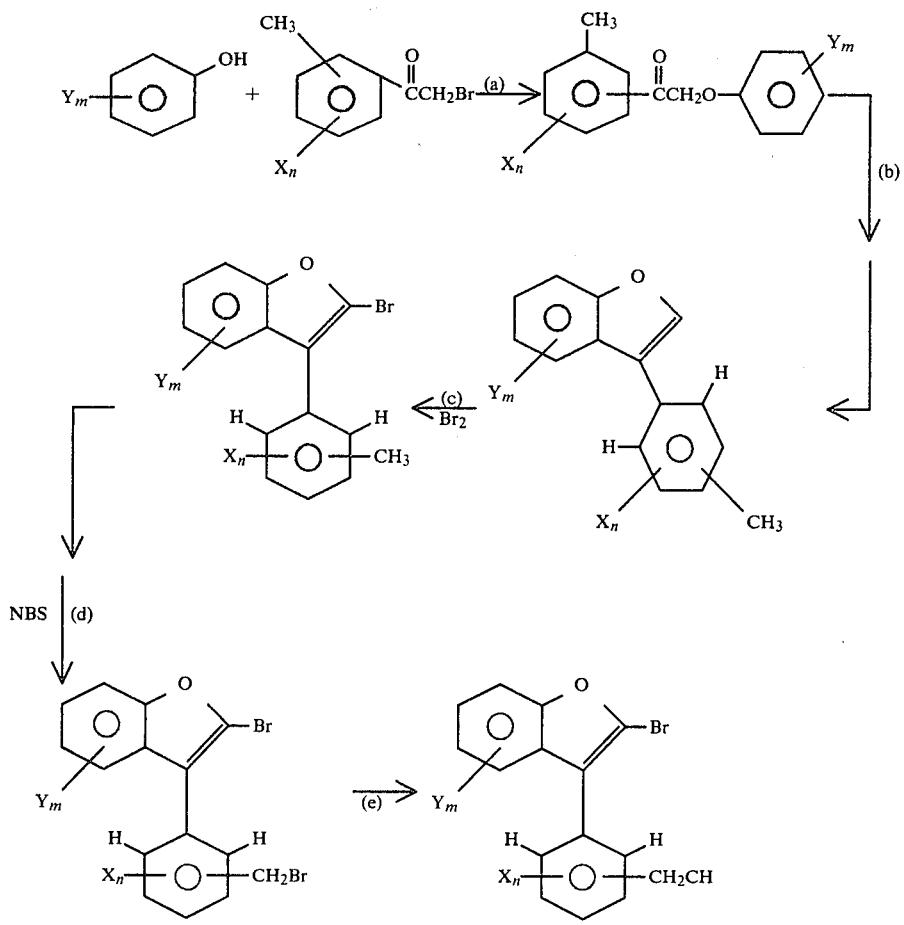

Steps (a) and (b) are analogous to steps ③ and ④ illustrated hereinabove, and are carried out as described earlier. The starting materials are known to the art.

Step (c) is the bromination of the furan ring using bromine water or preferably bromine in a suitable solvent such as dichloromethane, carbon tetrachloride or acetic acid.

Step (d) requires bromination of the methyl group with N-bromosuccinimide under free-radical conditions such as are known to the art.

Step (e) is reaction of the bromomethyl group with an alkali metal cyanide to give a cyanomethyl group. The 2-bromo substituent may be displaced by nitro either before conversion to the cyanomethyl derivative or before or after hydrolysis of the cyano group to an acid group.

The intermediate compounds of the formula

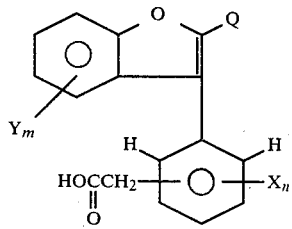

wherein X is halogen, lower alkyl, lower alkoxy or trifluoromethyl, Y is methyl, methoxy or halogen and m and n are independently zero, one or two, and Q is hydrogen, bromine or iodine, or an ester or pharmaceutically acceptable salt thereof are novel.

The salts of the free acid compounds of the invention are readily prepared by reaction of the acid with a base and evaporation to dryness. The base used to prepare the salts may be organic, e.g. sodium methoxide or an amine, or inorganic. Furthermore, other salts which are not pharmaceutically acceptable may be useful for the synthesis of the free acid compounds or other acceptable salts or other useful intermediates such as esters. The free acids can also be prepared from the corresponding esters by methods known to those skilled in the art.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative bacteria. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli,* Streptococcus sp. (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intraperitoneally with the test culture. Treatment consists of three oral injections 1, 6 and 24 hours after infection. All mice are observed for extended periods, e.g. for two weeks and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing an object to be treated therein, or by local application to an infected area. The amount of compound to be used for, e.g. oral treatment of a microbial infection will be an effective amount less than a toxic amount. The amount to be administered to a subject and route of administration to control an infection will depend on the species of organism, the sex, weight, physical condition of the patient, the locus of the infection and many other factors, but this judgment is well within the skill of the art. Usually the amount will be less than 100 mg/kg per dose. Conveniently the oral treatment is administered in the form of one of the usual pharmaceutical preparations such as capsules, tablets, emulsions, solutions, suppositories and the like. Excipients, fillers, coatings, etc., are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

Certain of the compounds are also active antiparasitics as shown by activity in laboratory tests versus the protozoan Trichomonas sp. In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. Thus, while the majority of the examples relate to the free acid compounds, the other compounds of the invention can also be prepared. The melting points are uncorrected, the temperatures are in degrees Centigrade and the pressures in millimeters of mercury.

EXAMPLE 1

Step A

To a mixture of 5 liters of dichloroethane and 798 g (6.0 mole) of aluminum chloride is added 492.6 g (3.0 mole) of ethyl phenylacetate. This solution is maintained at a temperature of 37°–40° C. while adding 471 g (6.0 mole) of acetyl chloride over a period of 3 hrs. The reaction is stirred at 45° C. for an additional 20 hrs. The reaction is added to an ice water mixture, the organic layer is separated, dried over magnesium sulfate, then evaporated to provide a residual oil. The oil is distilled under vacuum. Several fractions are collected boiling between 100°–130° C. at 0.1 mm of mercury pressure. Fractions which crystallize are recrystallized from petroleum ether. A solid is obtained which is shown to be ethyl (4-acetyl)phenylacetate, m.p. 56°–58.5° C. The structural assignment is confirmed by infrared and nuclear magnetic resonance spectral analysis.

Step B

To a solution of 14.7 g (0.07 mole) of ethyl (4-acetyl)phenylacetate in 150 ml of dichloromethane is added 11.4 g (0.071 mole) of bromine in 25 ml of dichloromethane over about 1.5 hours. The mixture is washed with a 5% solution of sodium acetate in water, then dried over magnesium sulfate. The solution is evaporated to provide an orange oil. Nuclear magnetic resonance spectral analysis of this oil indicates that it is chiefly the desired product, ethyl [4-(α-bromo)acetyl]phenylacetate.

Step C

A mixture of 20.2 g (0.071 mole) of ethyl [4-(α-bromo)acetyl]phenylacetate, 9.4 g (0.10 mole) of phenol, 20.0 g (0.145 mole) of potassium carbonate and 150 ml of benzene is heated to its reflux temperature and maintained at reflux for about 1 day. The mixture is then filtered, the filtrate is washed with water, cold sodium hydroxide solution, water again, and saturated sodium chloride solution, then dried over magnesium sulfate. The filtrate is then evaporated to provide a dark oil. Nuclear magnetic resonance spectral analysis of this compound shows it to be predominantly the desired product, ethyl [4-(α-phenoxy)acetyl]phenylacetate.

Step D

Polyphosphoric acid (350 g) is heated to 50° C. and stirred while adding 17.0 g (0.057 mole) of ethyl [4-α-phenoxy)acetyl]phenylacetate. After heating and stirring for about 2 hours, the mixture is poured into cold water. An oil separates and is taken up in diethyl ether. The ether solution is washed with water and saturated sodium chloride solution, and dried over sodium sulfate. The solution is then evaporated to provide a dark oil. The product is purified by elution chromatography on a silica gel column, eluting with chloroform-hexane mixtures. The first fraction is a pale yellow oil which is the desired product, ethyl 4-(3-benzofuranyl)phenylacetate, according to nuclear magnetic resonance spectral analysis.

Step E

A mixture of 6.4 g (0.023 mole) of ethyl 4(3-benzofuranyl)phenylacetate, 64 ml of 90% aqueous ethanol and 19.2 g of sodium hydroxide dissolved in a minimal amount of water is heated to its reflux temperature and maintained at reflux for about 3 hrs. The mixture is evaporated to remove the ethanol, then diluted with water and diethyl ether. The aqueous layer is separated, then poured into dilute hydrochloric acid. The solid product is collected, washed with water, and dissolved in diethyl ether. The ether solution is washed with water and saturated sodium chloride solution, then dried over sodium sulfate. The ether solution is evaporated to provide an oily orange solid. This product is 4-(3-benzofuranyl)phenylacetic acid, according to infrared and nuclear magnetic resonance spectral analysis.

Step F

To a solution of 5.7 g (0.023 mole) of 4-(3-benzofuranyl)phenylacetic acid, 3.3 g (0.040 mole) of sodium acetate and 150 ml of dichloromethane is added 3.7 g (0.023 mole) of bromine in 25 ml of dichloromethane over 1 hour. The mixture is stirred for about 3 hrs., then washed with water, 10% sodium bisulfite solution, water and saturated sodium chloride solution, then dried over magnesium sulfate. The mixture is then evaporated to provide a yellow oil which is 4-(2-bromo-3-benzofuranyl)phenylacetic acid according to infrared spectral analysis.

Step G

To a solution of 6.7 g (0.020 mole) of 4-(2-bromo-3-benzofuranyl)phenylacetic acid, 2.5 g (0.030 mole) of cyclohexene in 150 ml of acetic acid is added dropwise 2.8 g (0.030 mole) of dinitrogen tetroxide in 20 ml of acetic acid. After six hours the mixture is poured into cold water. A yellow gum separates which is dissolved in diethyl ether. The ether is washed four times with water then extracted six times with 100 ml of cold 0.5 N sodium hydroxide solution. The basic extracts are warmed to evaporate any residual ether, then poured into cold dilute hydrochloric acid. The yellow product is separated by filtration and dissolved in dichloromethane. The dichloromethane solution is washed with water and saturated sodium chloride solution then dried over magnesium sulfate. The organic solution is then evaporated to provide a yellow powder. The product is 4-(2-nitro-3-benzofuranyl)phenylacetic acid which is recrystallized from aqueous ethanol, a benzene-hexene mixture, then isopropyl alcohol to provide yellow crystals, m.p. 175°–178° C.

| Analysis: | % C | % H | % N |
|---|---|---|---|
| Calculated for $C_{16}H_{11}NO_5$: | 64.6 | 3.7 | 4.7 |
| Found: | 64.6 | 3.8 | 4.7 |

Using the method of Example 1 and starting with appropriate known substituted ethyl phenylacetates and substituted phenols the following compounds of the invention are prepared.

Table I

| Example No. | Starting Materials | Final Product |
|---|---|---|
| 2 | 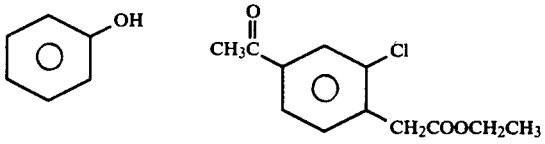 | 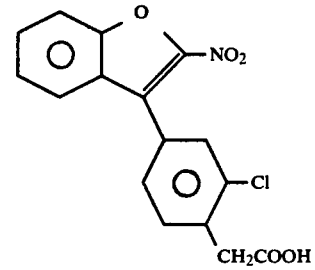 |
| 3 | 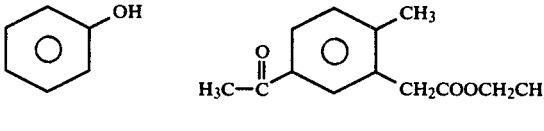 | 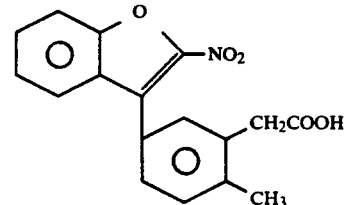 |
| 4 | 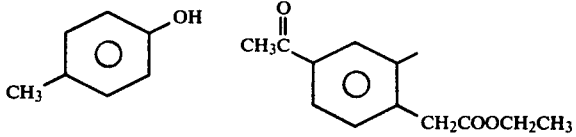 | 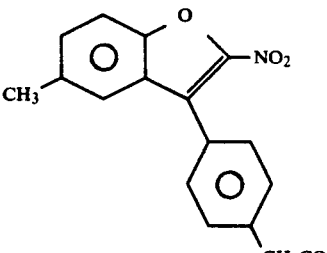 |

Table I-continued

| Example No. | Starting Materials | Final Product |
| --- | --- | --- |
| 5 | 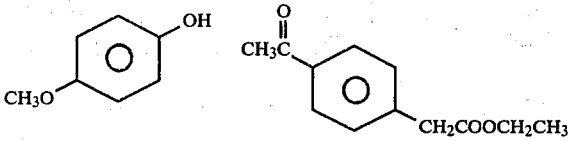 | 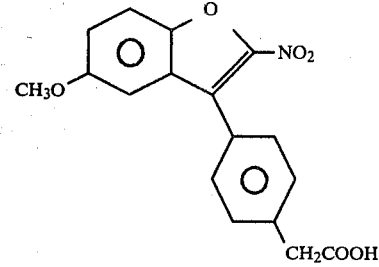 |
| 6 | 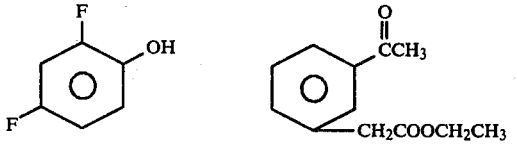 | 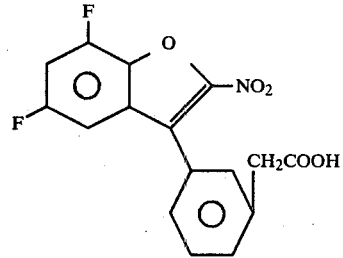 |
| 7 | 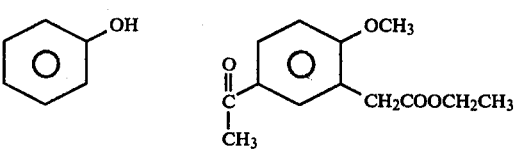 | 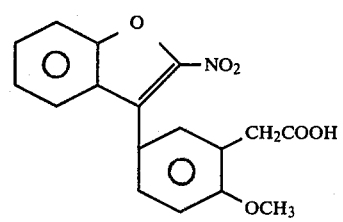 |

EXAMPLE 8

Step A

A mixture of 50 g (0.4 mole) of 4-chlorophenol, 89.2 g (0.4 mole) of 3-methyl -α-bromoacetophenone, 83 g (0.6 mole) of potassium carbonate and 500 ml of benzene is heated to its reflux temperature and maintained at reflux for about 20 hours while using a Dean-Stark trap to remove water. After cooling, the mixture is washed with water, 10% sodium hydroxide solution, 3 N hydrochloric acid, saturated sodium chloride solution and dried over magnesium sulfate. Evaporation of the solvent and trituration with hexane provides α-(4-chlorophenoxy)-3-methylacetophenone.

Step B

A mixture of 20 g of α-(4-chlorophenoxy)-3-methylacetophenone and 200 g of polyphosphoric acid is heated at 80° C. for about 30 hours. The reaction mixture is poured into water and stirred, then extracted with chloroform. The extracts are dried and evaporated to provide 5-chloro-3-(3-methylphenyl)benzofuran.

Step C

A solution of 19 g (0.078 mole) of 5-chloro-3-(3-methylphenyl)benzofuran in 500 ml of carbon tetrachloride is treated with 12.5 g (0.078 mole) of bromine over a period of 30 minutes. The reaction mixture is washed with water and dried over magnesium sulfate. The solvent is evaporated to provide a light brown oil which is analyzed by nuclear magnetic resonance spectra to confirm the structure as 2-bromo-5-chloro-3-(3-methylphenyl)benzofuran.

Step D

A mixture of 22.6 g (0.07 mole) of 2-bromo-5-chloro-3-(3-methylphenyl)benzofuran, 12.5 g (0.07 mole) of N-bromosuccinamide in 500 ml of carbon tetrachloride is irradiated and heated with a sun lamp for about 20 hours. The reaction mixture is filtered hot and the filtrate is allowed to cool. A solid forms which is collected, washed with carbon tetrachloride, and dried, then recrystallized from ethyl acetate to provide white product, 2-bromo-3-(3-bromomethylphenyl)-5-chlorobenzofuran, which is used directly in the next step.

Step E

The product of Step D, 2-bromo-3-(3-bromomethylphenyl)-5-chlorobenzofuran is reacted with sodium cyanide by heating to reflux in a solvent mixture of acetone and ethanol. Evaporation provides the desired product, 2-bromo-5-chloro-3-(3-cyanomethylphenyl)-benzofuran.

Step F

A solution of 2-bromo-5-chloro-3-(3-cyanomethylphenyl)benzofuran in aqueous ethanol and potassium hydroxide is heated to its reflux temperature and maintained at reflux for about 2 days. The solvent is removed by evaporation and the residue is dissolved in water and extracted with dichloromethane. The aqueous layer is acidified, then extracted with diethyl ether. The extracts are washed with water and saturated sodium chloride solution then evaporated to provide the product as a residue. The residue is recrystallized to provide 3-(2-bromo-5-chloro-3-benzofuranyl)phenylacetic acid.

Step G

A solution of 3-(2-bromo-5-chloro-3-benzofuranyl)-phenylacetic acid in chloroform with 1.5 equivalents of cyclonexene is treated with 1.5 equivalents of dinitrogen tetroxide and stirred for about 20 hours at room temperature. The mixture is washed with water, extracted with saturated sodium bicarbonate solution, then the aqueous extracts are acidified. The mixture is extracted with dichloromethane, which is dried and concentrated. The residue is recrystallized from a mixture of benzene and hexane to provide 3-(5-chloro-2-nitro-3-benzofuranyl)phenylacetic acid.

EXAMPLE 9

Step A

A mixture of 40 g (0.36 mole) of 4-fluorophenol, 80.3 g (0.36 mole) of 3-methyl-α-bromoacetophenone, 83 g (0.6 mole) of potassium carbonate in 500 ml of benzene is heated to its reflux temperature and maintained at reflux for 20 hours while removing water into a Dean-Stark trap. The reaction mixture is then washed with water, 10% sodium hydroxide solution, 3 N hydrochloric acid and saturated sodium chloride solution, then dried over magnesium sulfate. Evaporation of the solvent provides α-(4-fluorophenoxy)-3-methylacetophenone. The structure is confirmed by nuclear magnetic resonance spectral analysis. Using the method of Example 8 the above intermediate is converted to 3-(5-fluoro-2-nitro-3-benzofuranyl)phenylacetic acid.

What is claimed is:

1. A compound of the formula

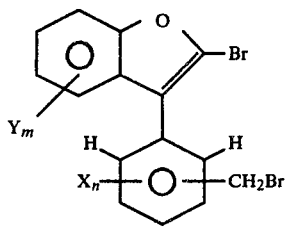

wherein X is halogen, lower alkyl, lower alkoxy or trifluoromethyl, Y is methyl, methoxy or halogen and m and n are independently zero, one or two.

2. The compound 2-bromo-3-(3-bromomethylphenyl)-5-chlorobenzofuran according to claim 1.

* * * * *